United States Patent [19]
McGlinch

[11] Patent Number: 6,068,121
[45] Date of Patent: May 30, 2000

[54] UNIVERSAL CATHETER TRAY

[75] Inventor: Timothy M. McGlinch, St. Paul, Minn.

[73] Assignee: Schneider (USA) Inc., Plymouth, Minn.

[21] Appl. No.: 09/038,072

[22] Filed: Mar. 11, 1998

[51] Int. Cl.[7] .................................................. B65D 83/10
[52] U.S. Cl. ........................ 206/364; 206/438; 206/560; 206/571
[58] Field of Search ................... 206/364, 363, 206/438, 525, 560, 561, 564, 565, 570, 571

[56] References Cited

U.S. PATENT DOCUMENTS

| | | | |
|---|---|---|---|
| 5,031,775 | 7/1991 | Kane | 206/364 |
| 5,178,267 | 1/1993 | Grabenkort et al. | 206/570 |
| 5,284,244 | 2/1994 | O'Toole et al. | 206/363 |
| 5,402,886 | 4/1995 | McGlinch | |
| 5,526,928 | 6/1996 | Yabe et al. | 206/364 |
| 5,568,865 | 10/1996 | Mase et al. | 206/438 |
| 5,848,691 | 12/1998 | Morris et al. | 206/364 |

*Primary Examiner*—David T. Fidei
*Assistant Examiner*—Luan K. Bui
*Attorney, Agent, or Firm*—Westman, Champlin & Kelly, P.A.

[57] ABSTRACT

A generally flat packaging tray for containing an elongated catheter device in an ordered coiled arrangement includes a recessed channel system formed within and including a plurality of spaced generally parallel, level, generally linear channel sections of two different depths joined by a plurality of arcuate channel sections some of which are inclined between the two depths and configured to contain catheter devices of a variety of lengths and french sizes nested therein in a coiled arrangement has an integral retention system of gently curved minor cantilever segments formed in the channel system that cooperate with inherent natural coil resisting resilience in a catheter shaft to benignly retain the catheter in the channel system.

15 Claims, 7 Drawing Sheets

UNIVERSAL CATHETER TRAY

BACKGROUND OF THE INVENTION

I. Field of the Invention

The present invention is directed generally to storage containers for packaging rather delicate flexible, elongate devices, particularly intravascular catheters, in coiled arrangement for shipment and prior to use. The invention more specifically relates to a packaging tray that benignly retains intravascular catheters, particularly delivery catheters, in a variety of french sizes and lengths in predetermined arrangement yet facilitates both the packing and removal of the devices in a manner that reduces the risk of damage to the catheter. The packaging tray of the invention can be inexpensively molded as a unitary piece preferably from transparent polymeric material that enables packaged devices to be identified prior to opening.

II. Related Art

Intravascular catheters vary widely in length from about 100–120 cm to lengths up to 255 cm or more. These devices usually contain one or more internal lumens traversing this length. These devices are somewhat flexible, but are relatively thin and easily kinked if overflexed. Kinking of the devices, of course, may close or impede one or more of the internal lumens rendering the device unusable. Traditionally, intravascular catheters of many types have been packaged supported on long cardboard backing "cards" contained in sterile plastic wrap and a plurality of these are, in turn, packaged in stacked fashion in a paperboard box or the like which typically contains up to five catheters. Removal of the catheters from the box and from the plastic wrap on the cards can be awkward owing in part to the rather long thin nature of the catheter and damage during either operation historically has occurred too frequently.

An improved storage container or box which facilitates removing the catheter packages is illustrated and described in U.S. Pat. No. 5,402,886 to McGlinch, the inventor of the present invention, and assigned to the same assignee as the present invention, which solves part of the problem, however, improvements in the packaging of the catheter itself are also needed and these have only partially been met.

More recently, intravascular catheter devices have been packaged by being arranged in recesses in relatively flat covered trays which are dedicated to specific diameters or french sizes and lengths. With some arrangements, the elongated catheter bodies and dedicated distal working or delivery sections are retained in place snugly in recessed tray channels held by retention clips. While they successfully retain the catheters, the clips make loading and removal of the catheters inconvenient and have also shown a decided propensity to induce kinks in the catheter delivery system tubes, particularly during the removal process, which destroys their usefulness.

Clip-free systems have also been introduced. One of these is illustrated in FIGS. 1a and 1b which depict at 10 a shallow generally rectangular packaging tray characterized by an elevated perimeter edge 12 and a system of recessed channels formed within the perimeter of the tray. The channels are all of a common depth and include spaced, generally straight and parallel side channels 14 and 16 joined by end arcuate segments 18 and 20; one or more additional arcuate segments as at 22 and 24 are provided connecting the side channels and running generally parallel to end arcuate segment 18. As series of spaced short, integrally molded retention overhang or cantilevered corner segments are provided at 26, 28, 30 and 32 and a plurality of side segments are provided at 34. A shaped recess 36 is provided for the valve body. The straight section 16 is intended to accommodate the stainless steel tube extension attached to the proximal end of the catheter to which the valve body is attached. This can be seen best in FIG. 1a, the bottom of the channels 18–24 and particularly 18 and 20 are rounded and dedicated to receive a particular size or narrow range of french sizes of catheters. In addition, the overhang, depicted by 38, of the corner cantilevered retainers is quite pronounced and extends a significant distance into the channel.

While the tray of FIGS. 1a and 1b has generally been successful, it does have certain limitations and drawbacks that are significant. The channel arrangement limits the variety of catheter lengths which can be successfully stored to those which are within a narrow range of lengths storable in one pass about the tray and which do not require the distal segment to be stored as a straight section. In addition, as mentioned, the corner overhangs are significant. While the amount of the channels covered by the overhangs, as at 38, is not a particularly significant drawback in packing or loading the catheter into the tray, difficulties with this characteristic become apparent when one seeks to remove the catheter from the tray perhaps several months later. The catheters are somewhat flexible but tend to return to an established retained memoried shape. Thus, when a catheter is first wound or coiled in a fashion to fit into the peripheral channel of the tray, the coil is given potential or stored energy which tends to straighten it again. This causes the device to recoil against the exterior walls of the channels where it is retained by the cantilevers. After a period of time in storage, a catheter device then becomes set in the coiled position and, in order to remove the catheter from the tray, each of the corner overhangs now has to be avoided by urging or distorting the catheter shaft inward. In doing so, there is a danger of over-flexing or snagging and causing kinks in the catheter shaft.

Thus, there remains a need for an improved catheter packaging system that particularly facilitates removal of the packaged catheter thereby reducing the tendency or propensity of the devices to incur damage prior to use. A need is also present for a catheter packaging tray that can accommodate a wide variety of catheter french sizes and lengths and including delivery catheters that require a linear distal storage arrangement.

Accordingly, it is a primary object of the present invention to provide a packaging tray for storing an intravascular catheter device which allows easy loading and removal of the catheter without danger of kinking.

Another object of the present invention is to provide a catheter package that accommodates a wide variety of diameter (french sizes) and lengths of intravascular catheter devices.

Still another object of the present invention is to provide a catheter packaging tray that enables direct liftout of the catheter from the package.

A further object of the present invention is to provide a catheter packaging tray having the above attributes and advantages that is of a one-piece or unitary design.

A still further object of the present invention is to provide a one piece catheter packaging tray having the foregoing advantages that is transparent so that the contained catheter device can be readily identified without opening the package.

Other objects and advantages will become apparent with familiarity with the specification, drawings and appended claims.

SUMMARY OF THE INVENTION

The present invention solves many of the problems associated with prior catheter packaging systems by providing a universal catheter tray formed in a single piece and able to accommodate a relative wide range of french sizes and all known lengths and which employs an integral and user friendly retention concept that enables easy coiling and packaging and permits direct lift-out of the device from the tray for use. The tray is a relatively flat, preferably generally rectangular-shaped container characterized by an elevated edge defining the perimeter of the tray and a system of recessed channels formed within the perimeter of the tray at several depths to contain the catheter device and accommodate devices of a variety of lengths and french sizes.

In one detailed embodiment, spaced parallel first and second, generally linear and generally parallel, longitudinal channels are provided in the tray generally extending along the length of the tray at a common first depth. The first channel is flanked by a closely spaced, generally parallel third, generally straight or linear channel having a second depth shallower than the first. The three parallel channels are joined at one end by an arcuate channel at the second depth and are joined at the other end by a ramped and arcuate channel which is gently inclined from the first depth to said second depth. A recess is provided to accommodate a variety of valve bodies at the first depth and a short bottom ramp is provided between the first channel and the level end arcuate channel. Retention cantilevers are provided along the outer edge of the second and third substantially straight parallel outer channels and single retention cantilevers of the same type are provided toward the central portion of each arc. A molded snap-in arrangement is further provided for containing the valve body stem. By using the appropriate connecting arc, a catheter of any length can be accommodated so that the distal section nests in the shallow linear channel section to accommodate a delivery device such as a stent delivery system or an angioplasty system or other working system.

The integral, benign retention concept includes a series of minor or very slight cantilevers or overhangs of various design and dimension formed into the exterior, apical part of the second and third linear and arcuate channels. These may be formed by a mechanical die during the manufacture of the tray and so may take on many shapes. The cantilevers or overhangs are designed such as to cooperate with and also take advantage of the natural straightening tendency of a catheter when first coiled and the tendency of the device to assume a set in the new position over time. The slight and gentle curvature of the overhang enables the device to be removed from the tray at the time of use by simply being lifted out without need to avoid the overhang or be concerned with straightening recoil. In addition, the channels are made large enough to accommodate a variety of french sizes without inhibiting loading, retention or removal of the catheters owing to the non-confining nature of the improved retention system.

In use, the stainless steel extension for a catheter is placed in the first channel and positioned such that the valve body can be accommodated properly in the valve body recess. The catheter attached to the extension is then wound in basically spiral fashion and inserted along the tray peripheral channel system including the appropriate ramped arc commensurate with the length of the catheter such that the distal end of the catheter, including a stent delivery or other working system, may be placed in the shallower or third linear section. The inclined nature of the ramped arcs allows the more distal portion of the catheter to cross over the top of the stainless steel extension for additional passes or into the third or shallower straight segment and the subtle cantilevers of the sides and arc hold the catheter in place so that a cover may be applied.

The tray and cover may be manufactured from any suitable polymer material that can be conventionally formed and processed but is preferably transparent so that the particular packaged catheter can be readily identified without opening the package. The material should be one which will survive temperature changes and not readily crack or chip nor affect the materials packaged within. Polyester materials have been used and are particularly successfully used material is polyol-modified polyethylene terphthalate (PET) and particularly a glycerin modified PET material known as PETG. The tray is designed to be typically covered by a piece of lid stock that is mechanically joined to the elevated peripheral edge of the tray. One successfully used lid material is a modified polyethylene such as Tyvek™.

While the size of the trays may vary, one model is approximately 19.0 inches (48.26 cm) in length and 7.75 inches (19.7 cm) in width and about 0.5 inches (1.27 cm) in depth. The perimeter of the tray is identified by an elevated edge approximately 0.04 inches (0.1 cm).

BRIEF DESCRIPTION OF THE DRAWINGS

In the drawings wherein like numerals are utilized to designate like parts throughout the same:

FIGS. 2b and 2c represent side elevational views of the tray of FIG. 2a;

FIGS. 2d and 2e are end elevational views of the tray of FIG. 2a;

FIG. 3 is an enlarged fragmentary sectional view of a cantilever or overhang system of the invention taken along 3—3 of FIG. 2a.

DETAILED DESCRIPTION

Figure 1A:
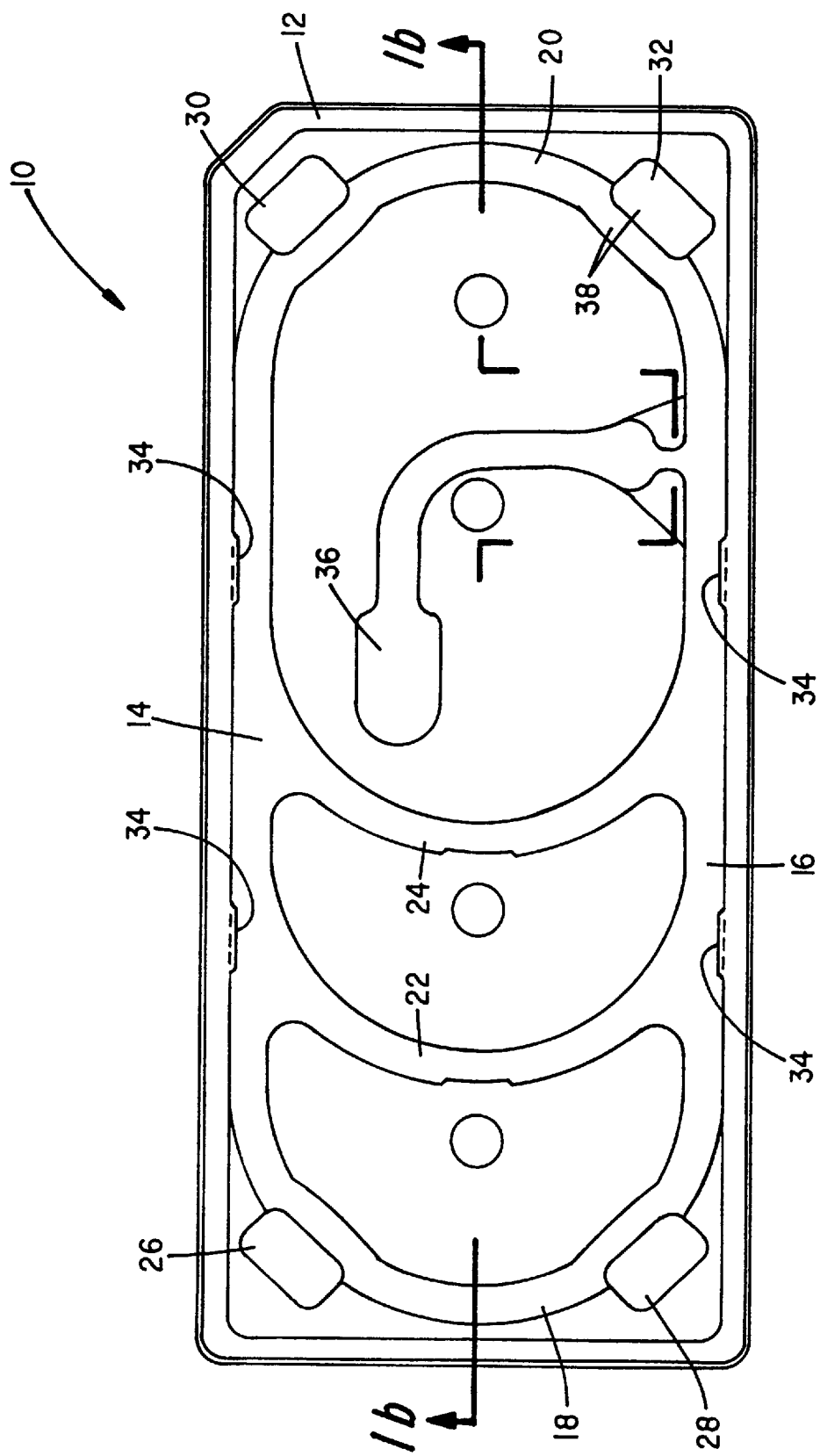
FIGS. 1a and 1b depict a prior art catheter tray of the class.
Figure 1B:
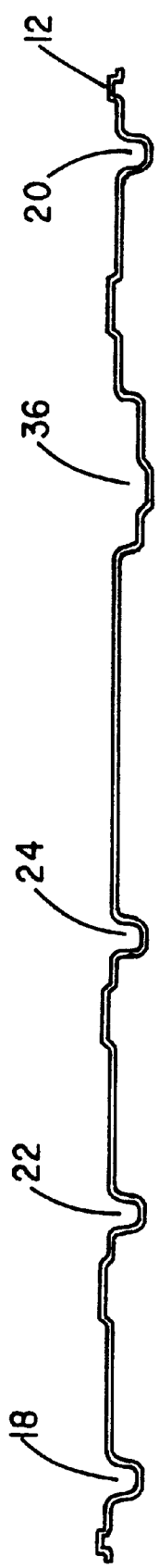
Figure 2A:
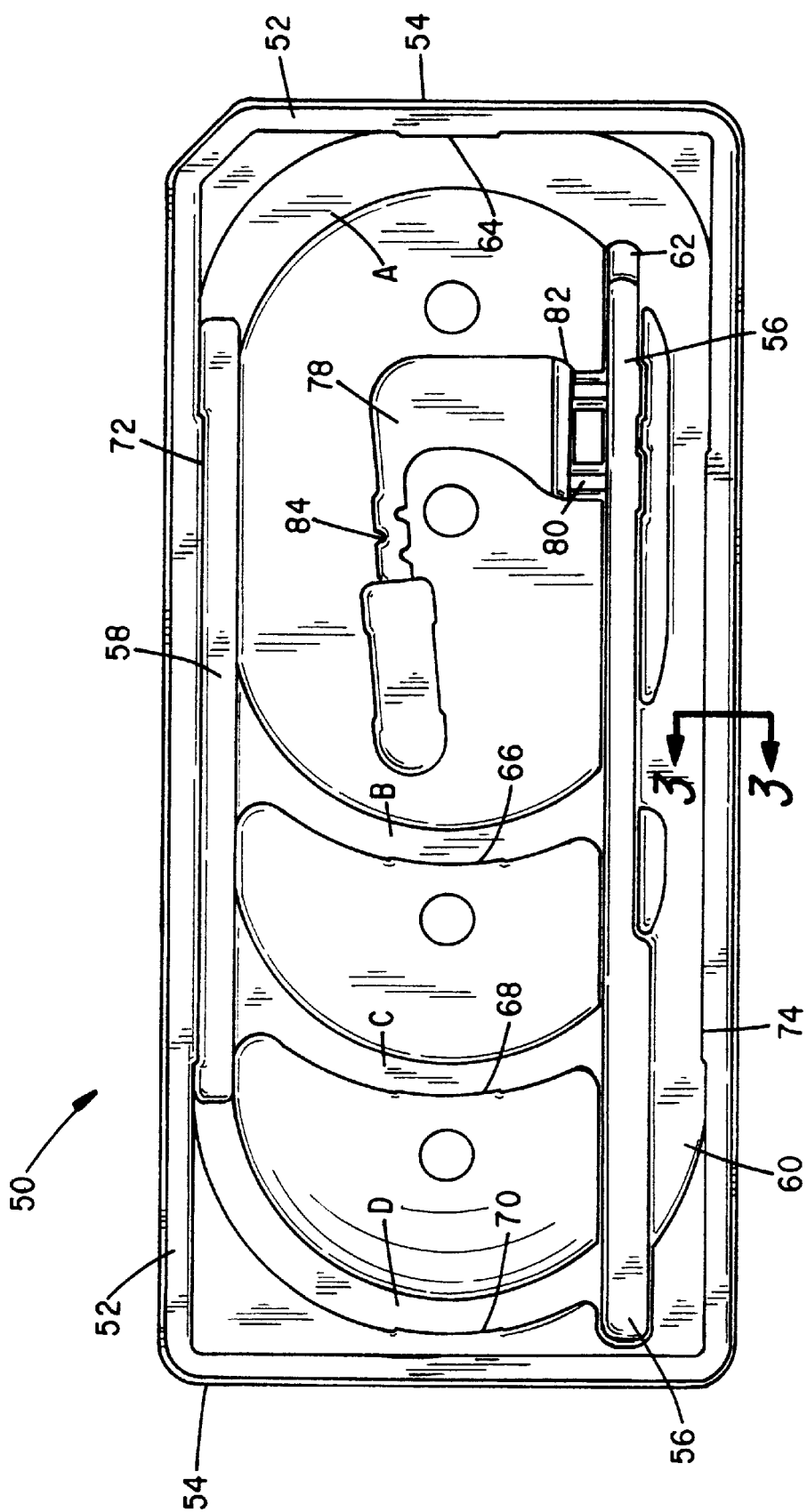
FIG. 2a represents a plan view of a tray in accordance with the present invention.
Figure 2B:
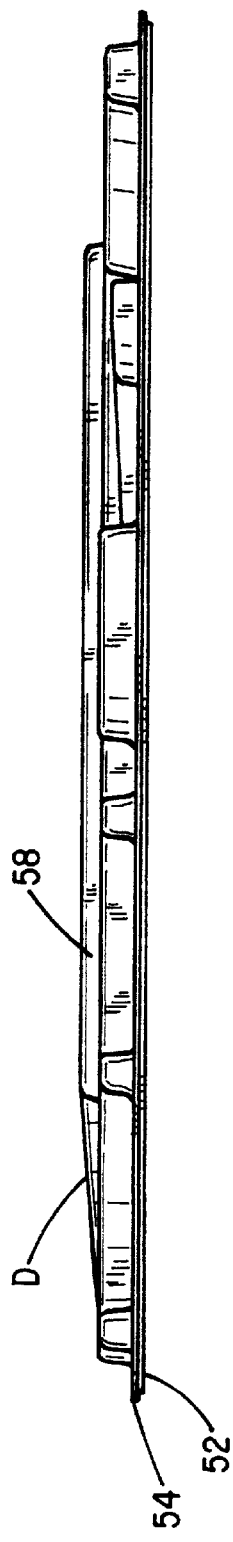
Figure 2C:
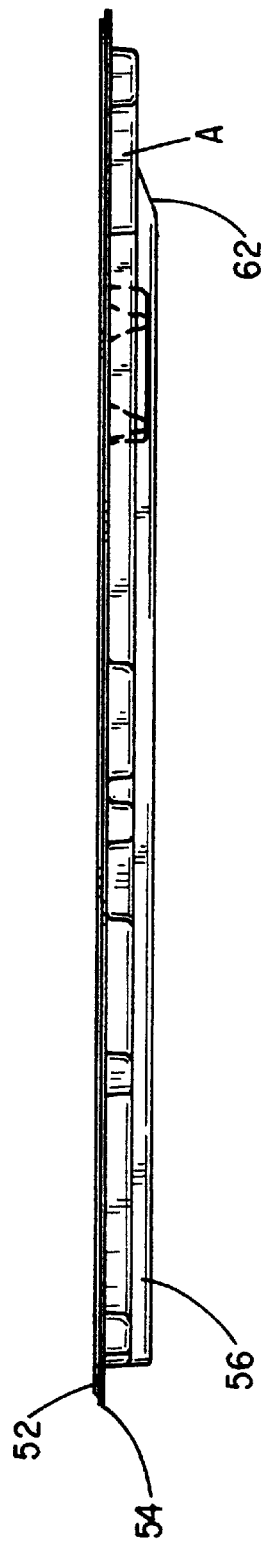
Figure 2E:
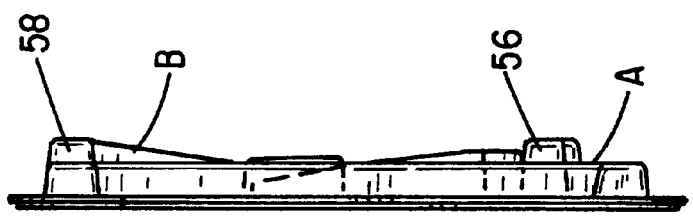
Figure 2D:
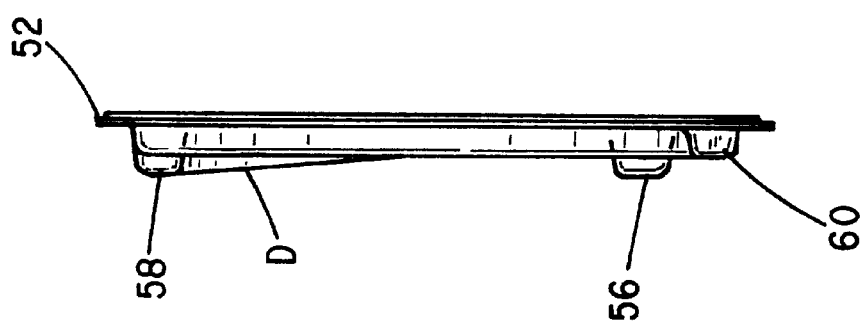

One embodiment of a universal catheter tray 50 configured in accordance with the invention is shown in the FIGS. 2a–2e in which FIG. 2a is a plan view, FIGS. 2b and 2c are opposite side elevational views and FIGS. 2d and 2e are end elevational views. The tray 50 is generally rectangular with an elevated perimeter edge 52 and a narrow perimeter edge lip 54 for receiving a compatible lid (not shown). The tray is provided with spaced, generally parallel, relatively deep recessed straight or linear channels sections 56 and 58. A third straight channel section 60, shallower than channels 56 and 58 is provided in close parallel relation to channel 56. A first end arcuate channel A is provided at the depth level of channel section 60 joining one end of the straight channel sections 56, 58 and 60. A short ramp 62 is provided between arcuate section A and channel section 56. A second end arcuate channel section D, together with intermediate, generally parallel curved channel sections B and C are provided which, as can be seen in FIGS. 2b and 2d are ramped or inclined upward from the depth of channel 58 to that of channel 60.

Figure 3:
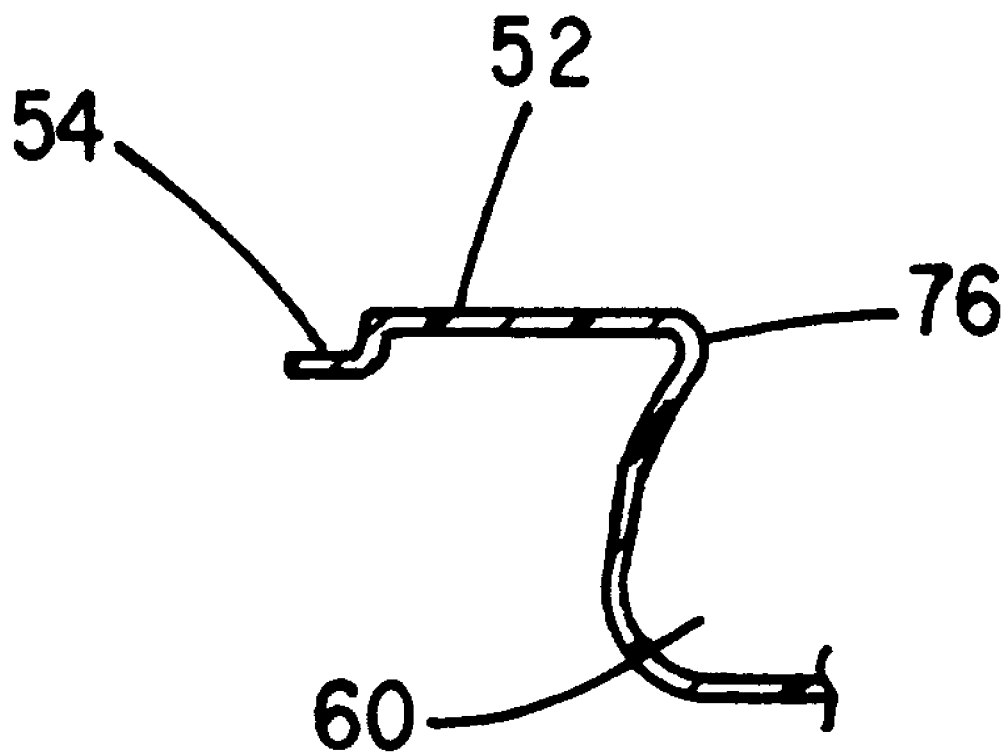

Each of the arcuate channel or passage sections A–D are further provided with very subtle or modest overhang or cantilever segments, generally centrally located in the tray respectively, at 64, 66, 68 and 70. The outer sides of channels 58 and 60 are also provided with extended overhangs or cantilevers as at 72 and 74. A typical cantilever is best illustrated at 76 in the fragmentary sectional view of FIG. 3. The gradual nature of the curve defining the overhang or cantilever structure allows direct lift-out of a packaged catheter upon removal of the lid, yet has been found to provide sufficient restraint for proper retention of catheters of a range of french sizes.

The universal tray of the invention further includes a recess 78 designed to accommodate a valve body associated with the catheter and is provided with several recessed connector accesses to channel section 56 at 80 and 82. A snap-in zig-zag section 84 is provided to retain a variety of extension tubes and connected valve bodies in place.

Figure 4:
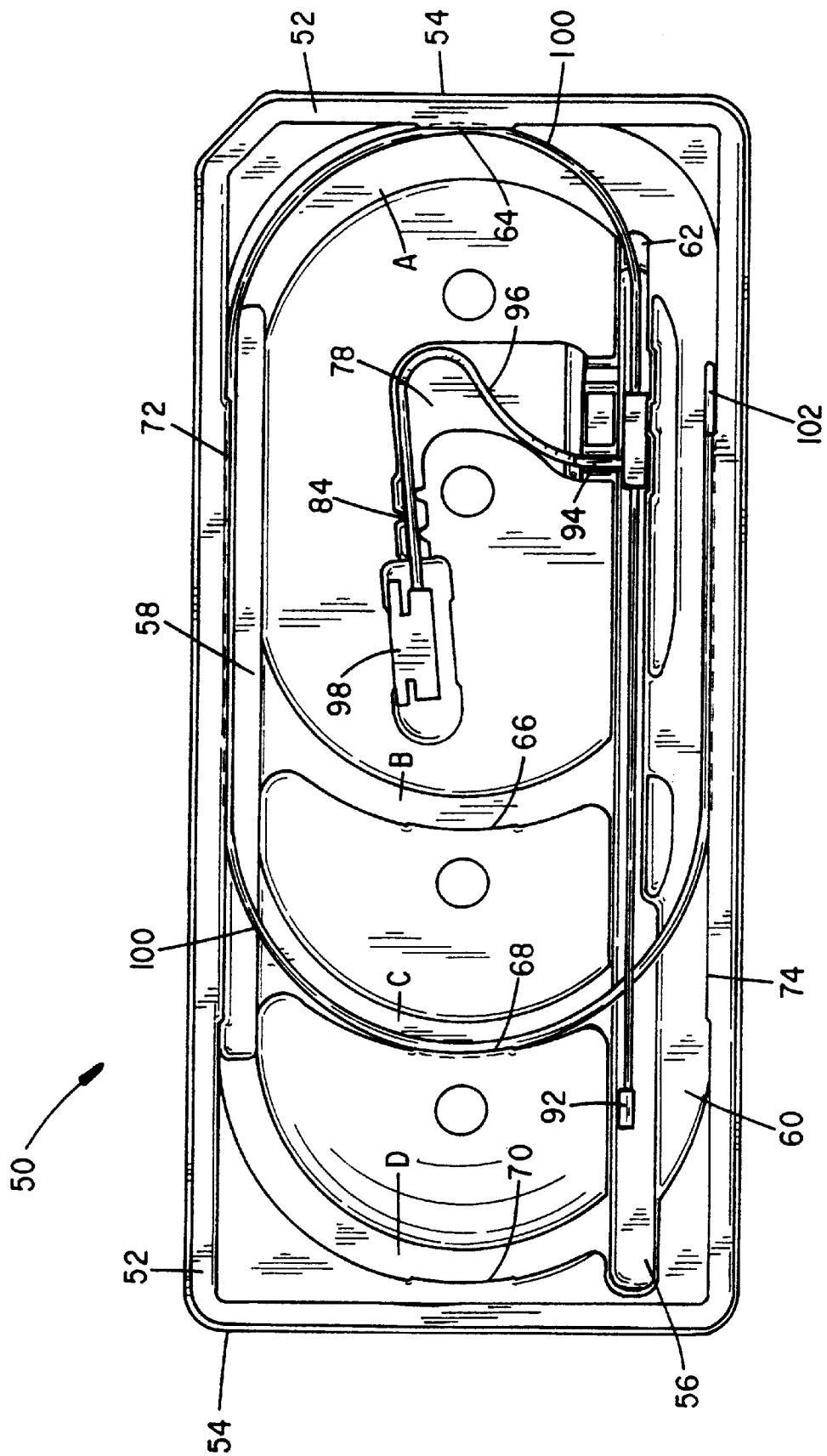
FIG. 4 is a plan view similar to FIG. 2a that further depicts a catheter device loaded in the tray.

FIG. 4 is a view similar to FIG. 2a with the addition of a catheter device 90 of the class to be packed in such trays shown in the loaded or packed position in the tray 50. The catheter includes extension tube 92 with valve body connection 94 snapped into access 80 and connected by 96 to a valve body or system 98. The catheter body 100 is of a length to utilize curved channel sections A and C the distal section of the catheter ending with a straight delivery system nested in channel 60 at 102. The catheter 80 is shown expanded against the outer walls of the tray channels as discussed above.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A generally flat packaging tray for containing an elongated catheter device in an ordered coiled arrangement comprising:
   (a) a recessed channel system formed within and including a plurality of spaced generally parallel, level, generally linear channel sections of first and second depths joined by a plurality of arcuate channel sections some of which are inclined between said first and said second depths and configured to contain a catheter device nested therein; and
   (b) integral retention system comprising gently curved minor cantilevers formed in said channel system that cooperate with inherent natural coil resisting resilience in a catheter shaft to benignly retain said catheter in said channel system.

2. The packaging tray of claim 1 wherein said cantilevers are employed along a central region of the arcuate portions of said channel system.

3. The packaging tray of claim 1 wherein said recessed channel system further comprises:
   (1) first and second spaced generally parallel straight generally linear channel segments extending lengthwise of the tray at a common first depth;
   (2) third generally linear channel segment beyond and flanking and generally parallel to said second channel and having a second depth shallower than the depth of said second channel;
   (3) a relatively level arcuate end channel joining one end of the first, second and third parallel channels at said second depth;
   (4) a ramped end arcuate channel joining said first and third parallel linear channels at another end, said first ramped arcuate channel being gently inclined from said first depth to said second depth; and
   (5) one or more additional ramped, arcuate channels intermediate the end arcuate channels and generally parallel to said ramped arcuate end channel.

4. The packaging tray of claim 3 wherein said cantilevers are substantially continuous along an outer edge of the first and third linear channel straight segments.

5. The packaging tray of claim 1 wherein said each channel of said recessed channel system has a crossection of sufficient size to accommodate a variety of catheter diameters.

6. The packaging tray of claim 4 wherein said each channel of said recessed channel system has a crossection of sufficient size to accommodate a variety of catheter diameters.

7. The packaging tray of claim 1 further comprising a covering lid configured to be mechanically joined to said tray.

8. The packaging tray of claim 1 wherein the tray is transparent.

9. The packaging tray of claim 8 wherein said tray is fabricated from glycerine modified polyethylene terephthalate.

10. The packaging tray of claim 1 further comprising a recess including snap-in connector receiver to accommodate a catheter valve body stem.

11. The packaging tray of claim 4 wherein said second generally linear channel segment is dedicated to separately receive only a catheter extension tube, said packaging tray further comprising a valve body recess for receiving a valve body connected to the catheter extension tube, said recess being connected by cross channel to said second generally linear channel segment at at least one location.

12. The packaging tray of claim 11 wherein said valve body recess is connected by cross channel to said first linear channel at a plurality of spaced locations to accommodate a plurality of extension tube lengths.

13. The packaging tray of claim 12 further comprising snap fit system for holding a valve body stem in said valve body recess.

14. The packaging tray of claim 1 wherein one of said generally linear channel sections is dedicated to carry only a catheter extension tube.

15. A generally flat packaging tray for containing an elongated catheter device having an extension tube and valve body in an ordered coiled arrangement comprising:
   (a) a recessed channel system formed within and including a plurality of spaced generally parallel, generally linear channel sections joined by a plurality of arcuate channel sections and configured to contain a catheter device nested therein;
   (b) integral retention system comprising gently curved minor cantilevers formed in said channel system that cooperate with inherent natural coil resisting resilience in a catheter shaft to benignly retain said catheter in said channel system;
   (c) wherein one of said generally linear channel sections is dedicated to receive only a catheter extension tube;
   (d) a valve body recess in said packaging tray for receiving a valve body connected to said catheter extension tube; and
   (e) wherein said generally linear channel sections are at a plurality of depths to accommodate non-interfering crossover of said elongated catheter in relation to said extension tube.

* * * * *